(12) United States Patent
Loneragan et al.

(10) Patent No.: US 10,114,019 B2
(45) Date of Patent: *Oct. 30, 2018

(54) BACTERIAL CHALLENGE MODEL IN CATTLE USING A TRANS- AND INTRA-DERMAL ROUTE TO INFECT PERIPHERAL LYMPH NODES

(71) Applicants: Texas Tech University System, Lubbock, TX (US); United States Department of Agriculture, College Station, TX (US)

(72) Inventors: Guy Loneragan, Lubbock, TX (US); Thomas Edrington, College Station, TX (US)

(73) Assignees: TEXAS TECH UNIVERSITY SYSTEM, Lubbock, TX (US); THE UNITED STATES OF AMERICA AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/196,582

(22) Filed: Mar. 4, 2014

(65) Prior Publication Data

US 2014/0248605 A1 Sep. 4, 2014

Related U.S. Application Data

(60) Provisional application No. 61/772,119, filed on Mar. 4, 2013.

(51) Int. Cl.
| | |
|---|---|
| *G01N 33/569* | (2006.01) |
| *G01N 33/50* | (2006.01) |
| *A61M 5/19* | (2006.01) |
| *A61M 5/178* | (2006.01) |
| *A61K 39/112* | (2006.01) |

(52) U.S. Cl.
CPC ... *G01N 33/56916* (2013.01); *A61K 39/0275* (2013.01); *A61M 5/178* (2013.01); *A61M 5/19* (2013.01); *G01N 33/5088* (2013.01); *G01N 33/569* (2013.01); *A01K 2267/03* (2013.01)

(58) Field of Classification Search
None
See application file for complete search history.

(56) References Cited

U.S. PATENT DOCUMENTS

| | | | |
|---|---|---|---|
| 4,205,689 A | 6/1980 | Brennan | |
| 4,222,392 A | 9/1980 | Brennan | |
| 5,104,620 A | 4/1992 | Wiley et al. | |
| 5,637,303 A * | 6/1997 | Radford | C07K 14/34 424/200.1 |
| 6,776,776 B2 * | 8/2004 | Alchas | A61M 5/3129 604/117 |
| 2002/0076417 A1 * | 6/2002 | Mahan | A61K 39/025 424/200.1 |
| 2005/0163711 A1 * | 7/2005 | Nycz | A61K 9/0021 424/9.1 |

FOREIGN PATENT DOCUMENTS

EP 0407063 * 6/1990

OTHER PUBLICATIONS

Lonergan et al. Solutions for the food Safety threat posed by *Salmonella* in the Lymph nodes of Cattle presented for harvest. May 2012 (published 2011).*
Mohler et al. Vaccine (2008) 26,1751-1758.*
Neutra et al. Nat Rev Immunol. Feb. 2006;6(2):148-158.*
Xujie et al. Microbiol Immunol 2011; 55:254-266.*
Arthur, T. M., et al., 2008 "Prevalence and characterization of *Salmonella* in bovine lymph nodes potentially destined for use in ground beef" J. Food Prot. 71:1685-1688.
Dodd, C. C., et al., 2011 "Evaluation of the effects of a commercially available *Salmonella* Newport siderophore receptor and porin protein vaccine on fecal shedding of *Salmonella* bacteria and health and performance of feedlot cattle" Am. J. Vet. Res. 2:239-247. [Abstract].
Edrington, T. S., et al., 2008 "Prevalence of multidrug-resistant *Salmonella* on commercial dairies utilizing a single heifer raising facility" J. Food Prot. 71:27-34. [Abstract].
Edrington, T. S., et al., 2009 "Influence of sprinklers, used to alleviate heat stress, on faecal shedding of *E. coli* O157: H7 and *Salmonella* and antimicrobial susceptibility of *Salmonella* and Enterococcus in lactating dairy cattle" Lett. Appl. Microbiol. 48:738-743.
Edrington, T. S., et al., 2013 "Development of a transdermal *Salmonella* challenge model in calves" J. Food Prot. 76:1255-1258.
Farrow, R. L., 2012 "Quantitative herd-level evaluation of a commercially available vaccine for control of *Salmonella* in dairy cattle" Ph.D. dissertation. Texas A&M University, College Station.
Haneklaus, A. N., et al., 2012 "*Salmonella* prevalence in bovine lymph nodes differs among feedyards" J. Food Prot. 75:1131-1133.
Heider, L. C., et al., 2008 "Evaluation of vaccination with a commercial subunit vaccine on shedding of *Salmonella enterica* in subclinically infected dairy cows" J. Am. Vet. Med. Assoc. 233:466-469. [Abstract].

(Continued)

*Primary Examiner* — Oluwatosin A Ogunbiyi
(74) *Attorney, Agent, or Firm* — Edwin S. Flores; Daniel J. Chalker; Chalker Flores, LLP

(57) ABSTRACT

The present invention includes a method of observing and evaluating bacterial infections within the lymph nodes of animals presented for harvest comprising: inoculating at one or more sites of an animal a known amount of a pathogen, wherein the one or more inoculation sites comprise lymph node drainage areas, and at one or more time points obtaining one or more lymph node biopsies to determine the extent of the pathogen in the lymph nodes.

15 Claims, 3 Drawing Sheets

(56) References Cited

OTHER PUBLICATIONS

Hermesch, D. R., et al., 2008 "Effects of a commercially available vaccine against *Salmonella enterica* serotype Newport on milk production, somatic cell count, and shedding of *Salmonella* organisms in female dairy cattle with no clinical signs of salmonellosis" Am. J. Vet. Res. 9: 1229-1234.[Abstract].
Koohmaraie, M., J. A. et al., 2012 "Tracking the sources of *Salmonella* in ground beef produced from nonfed cattle" J. Food Prot. 75:1464-1468. [Abstract].
Loneragan, G. H., et al., 2012 "*Salmonella* diversity and burden in cows on and culled from dairy farms in the Texas high plains" Foodborne Pathog. Dis. 9:549-555.
U.S. Department of Agriculture, Food Safety and Inspection Service. 2010 "Progress report on *Salmonella* testing of raw meat and poultry products" 1998-2010. Available at: www.fsis.usda.gov/PDF/Salmonella_Progress_Report_1998-2003.pdf. Accessed Apr. 10, 2013.

\* cited by examiner

BACTERIAL CHALLENGE MODEL IN CATTLE USING A TRANS- AND INTRA-DERMAL ROUTE TO INFECT PERIPHERAL LYMPH NODES

CROSS-REFERENCE TO RELATED APPLICATIONS

This Non-Provisional patent application claims priority to U.S. Provisional Patent Application Ser. No. 61/772,119, filed Mar. 4, 2013, the contents of which is incorporated by reference herein in its entirety.

STATEMENT OF FEDERALLY FUNDED RESEARCH

This invention was made with U.S. Government support by the USDA grant number 2011-51110-31081. The government has certain rights in this invention.

TECHNICAL FIELD OF THE INVENTION

The present invention relates in general to the fields of immunology and microbiology, and more particularly, to a model for the development, study and use of a trans- and intra-dermal route to infect peripheral lymph nodes.

INCORPORATION-BY-REFERENCE OF MATERIALS FILED ON COMPACT DISC

None.

BACKGROUND OF THE INVENTION

Without limiting the scope of the invention, its background is described in connection with inoculation of large animals.

U.S. Pat. No. 4,205,689, issued to Brennan, for an allergy testing system that included a skin testing system for in vivo intracutaneous use that comprises a novel injection unit and multiple applicator, each of the units carrying biological or chemical substances for skin testing, at least one of the units carrying a plurality of different antigens in admixture. Test substances are deposited intracutaneously by piercing the skin with each injection to predetermined depth; and the pierced skin is observed for response to the various substances and dermographia.

U.S. Pat. No. 4,222,392, also issued to Brennan, for an allergy testing device with vented base. The patent is directed to an improved skin test kit comprising a base well and a plurality of injection units held in recessed depressions of the base and removable therefrom. A vent is provided that permits gas to escape during insertion of the injection units. The injection units comprise a hilt portion that may be mated with the periphery of the well depression. A vent hole communicating with a portion of the depression can vent gas through the base bottom, thereby preventing excessive pressure in the well.

U.S. Pat. No. 5,104,620, issued to Wiley, et al., is directed to a disposable allergy skin testing kit. Briefly, a disposable allergy skin testing kit is formed from a top layer sheet, a membrane sheet, and a bottom layer sheet. The bottom sheet has a plurality of recesses formed at predetermined locations to form chambers into which a predetermined antigen has been deposited. The membrane sheet covers these chambers and forms a liquid tight seal and the top layer sheet has an aperture formed in it above each of the antigen chambers. A push button needle assembly is mounted in each of these apertures and it has a disk-shaped pushbutton with a needle extending downwardly from its bottom surface.

SUMMARY OF THE INVENTION

In one embodiment, the present invention includes a method of observing and evaluating bacterial infections within the lymph nodes of animals presented for harvest comprising: inoculating at one or more sites of an animal a known amount of a pathogen, wherein the one or more inoculation sites comprise lymph node drainage areas; and at one or more time points obtaining one or more lymph node biopsies to determine the extent of the pathogen in the lymph nodes. In one aspect, the inoculation is subdermal or transdermal. In another aspect, the pathogen is selected from *Salmonella, Listeria, Shigella, Fransicella, Clostridum, Staphylococcus, Streptococcus*, or *Bacillus*. In another aspect, the lymph node drainage areas comprise at least one of subiliac, popliteal, retropharangeal, superficial cervical, and mesenteric. In another aspect, the pathogens are selected from at least one of viral, fungal, protozoan, helminthic pathogens. In another aspect, the animals comprise bovine, equine, ovine, porcine, or caprine. In another aspect, the pathogen is selected from *Salmonella* Newport and Montevideo.

In another embodiment, the present invention includes a method of observing and evaluating bacterial infections within the lymph nodes of animals presented for harvest comprising: inoculating at one or more sites of an animal a known amount of a pathogen, wherein the one or more inoculation sites comprise lymph node drainage areas; treating the animal with one or more therapies, treatments, or exposure; at one or more time points obtaining one or more lymph node biopsies to determine the extent of the pathogen in the lymph nodes; and determining if the one or more therapies, treatments, or exposure were effective to eliminate or reduce the pathogen. In one aspect, the wherein the inoculation is subdermal or transdermal. In another aspect, the wherein the pathogen is selected from *Salmonella, Listeria, Shigella, Fransicella, Clostridum, Staphylococcus, Streptococcus*, or *Bacillus*. In another aspect, the lymph node drainage areas comprise at least one of subiliac, popliteal, retropharangeal, superficial cervical, and mesenteric. In another aspect, the pathogens are selected from at least one of viral, fungal, protozoan, helminthic pathogens. In another aspect, the animals comprise bovine, equine, ovine, porcine, or caprine. In another aspect, the pathogen is selected from *Salmonella* Newport and Montevideo.

A method of testing a compound for elimination of bacterial infections within the lymph nodes of animals presented for harvest comprising: inoculating at one or more sites of an animal a known amount of a pathogen, wherein the one or more inoculation sites comprise lymph node drainage areas; treating the animal with one or more compounds; at one or more time points obtaining one or more lymph node biopsies to determine the extent of the pathogen in the lymph nodes; and determining if the compound was effective to eliminate or reduce the pathogen. In one aspect, the inoculation is subdermal or transdermal. In another aspect, the pathogen is selected from *Salmonella, Listeria, Shigella, Fransicella, Clostridum, Staphylococcus, Streptococcus*, or *Bacillus*. In another aspect, the lymph node drainage areas comprise at least one of subiliac, popliteal, retropharangeal, superficial cervical, and mesenteric. In another aspect, the pathogens are selected from at least one of viral, fungal, protozoan, helminthic pathogens. In another aspect, the animals comprise bovine, equine, ovine, porcine, or caprine. In another aspect, the pathogen is selected from *Salmonella* Newport and Montevideo.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Example 1: Development of a Trans- and Intra-Dermal Route of Inoculation

The present inventors developed a trans- and intra-dermal route of inoculation to challenge calves with bacteria such as *Salmonella*. A multi inoculator (e.g., lancet) allergy skin-testing device is inoculated with a *Salmonella* broth and applied with mild pressure to specific regions of the bovine's hide that are drained to region-specific lymph nodes. This process may be repeated at the time of initial inoculation or at subsequent days.

FIG. 1 shows one embodiment of the vaccination device for use with the present invention in which (in this example) 10 inoculation needles are shown. FIG. 2 shows the loading of vaccine into the inoculation needles. FIG. 3 shows a trans/intra dermal challenge site for inoculation to the lymph nodes. FIG. 4 shows the location of the inoculations and the lymph nodes from which the different strains of bacteria were recovered.

At various time-points after inoculation, the cattle are sacrificed and target lymph nodes are aseptically harvested and *Salmonella* is recovered and/or detected by culture and isolation or non-culture based detection assays. The method is applicable to many *Salmonella* serotypes and predictably results in *Salmonella*-positive lymph nodes. Inoculation of the hind leg results in *Salmonella* recovery from the Popliteal lymph node. Inoculation of the ventral abdomen results in *Salmonella* recovery from the Subiliac lymph node. Inoculation of the fore leg results in *Salmonella* recovery from the Prescapular lymph node.

The present inventors recognized that non-mesenteric lymph nodes in cattle may be a significant source of *Salmonella* contaminating ground beef. The objective of this work was to determine whether, e.g., a commercially-available *Salmonella* vaccine protects calves from lymph node colonization following significant oral challenge with two strains of *Salmonella* frequently isolated from dairy cattle, *Salmonella* Newport and Montevideo.

Briefly, thirty-two Holstein calves were purchased from a calf ranch in the panhandle of Texas and transported to a laboratory in College Station, Tex. One week following arrival (d 0), all calves were randomly assigned to treatment (Control or Vaccine; n=16 hd/treatment). Vaccinate calves were administered a commercially-available *Salmonella* Newport SRP vaccine (2 ml s.c.) while control calves received a sham-injection of corn oil (2 ml s.c.). A second booster vaccination and sham-injections were administered on d 21. Body weights were recorded weekly throughout the study period and rectal swabs collected at time of weighing on d 0, 7, 14, 21 and 28. On day 33, calves were assigned to pen (8 pens, 4 calves per pen) and inoculated *Salmonella* strain (Montevideo or Newport; 4 pens/strain). On d 35, all calves were inoculated with either *Salmonella* Montevideo or Newport resulting in four treatments: Control—Newport; Control—Montevideo; Vaccine—Newport; Vaccine—Montevideo; eight calves and two pens per treatment. On d 49 (14 d post-inoculation) one-half of the calves (Group 1) in each pen (and treatment) were euthanized and necropsied.

The following lymph nodes were collected and cultured for the challenge strains of *Salmonella*: subiliac (left and right), popliteal (left and right), retropharangeal, superficial cervical (left and right), and mesenteric (ileo-cecal). On d 56 (21 d post-inoculation), all remaining calves (Group 2) were euthanized and necropsied. All lymph nodes were quantitatively and qualitatively cultured for the challenge strains of *Salmonella*. Very few lymph nodes contained quantifiable populations. The percentages of *Salmonella*-positive lymph nodes following enrichment were much higher, although at 14-d post-inoculation (Group 1), no significant treatment differences were observed in the percentage of lymph nodes positive for *Salmonella* Montevideo or Newport. However at 21-d post-inoculation, there were fewer ($P<0.05$) right popliteal (0 versus 75%) and right pre-scapular nodes (0 versus 75%) that were *Salmonella* positive in the Vaccine—Newport compared to Control—Newport treatments. The percentage of left popliteal and left pre-scapular nodes likewise tended ($P=0.10$) to decrease in the Vaccine-Newport treatment compared to non-vaccinated controls, while more ileo-cecal lymph nodes tended ($P=0.10$) to be positive in the Vaccine-Newport treatment. *Salmonella*-positive mandibular nodes tended ($P=0.10$) to increase in the Vaccine—Montevideo treatment compared to Control—Montevideo calves. All fecal swabs, collected weekly for five weeks prior to *Salmonella* infection, were culture negative. Post-inoculation fecal samples were not affected by treatment ($P>0.05$) for either strain, although in Group 2 there was a tendency ($P=0.09$) for the Control-Newport calves to shed lower concentrations of *Salmonella* compared to the Vaccine-Newport animals. Initial and final body weights and overall body weight change were not different ($P>0.05$) due to treatment. While no treatment effects were observed in the Group 1 calves, the data from Group 2 suggests that the vaccine may have been more effective with additional time between initial infection and necropsy and/or a lower challenge dose of *Salmonella*.

Figure 1:
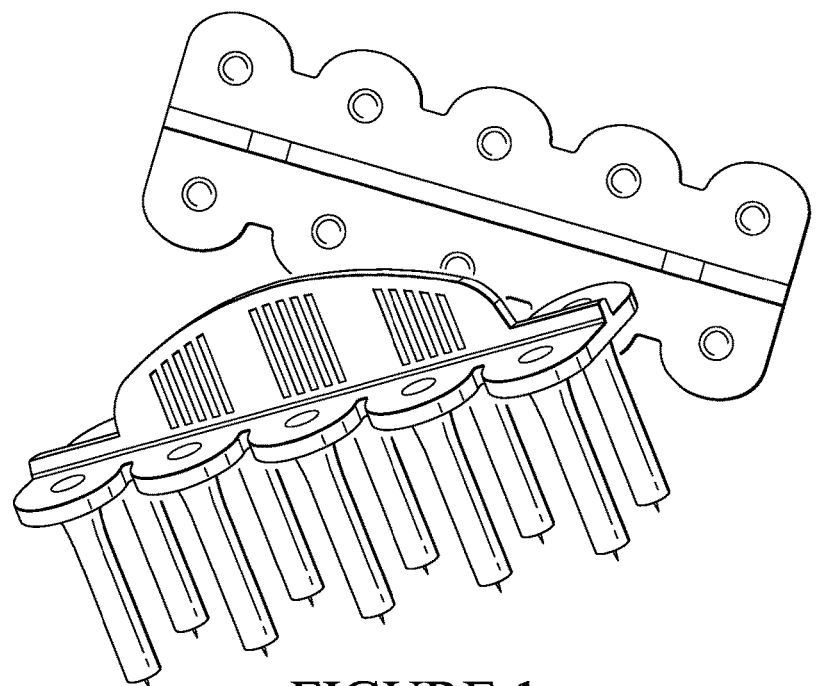
FIG. 1 shows one embodiment of the vaccination device for use with the present invention in which (in this example) 10 inoculation needles are shown.
Figure 2:
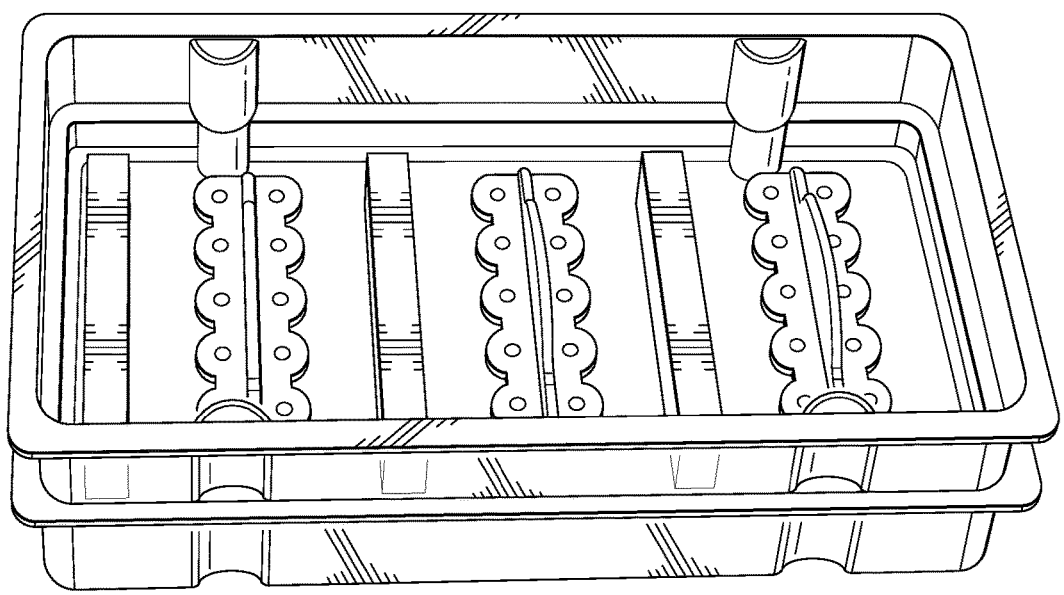
FIG. 2 shows the loading of vaccine into the inoculation needles.
Figure 3:
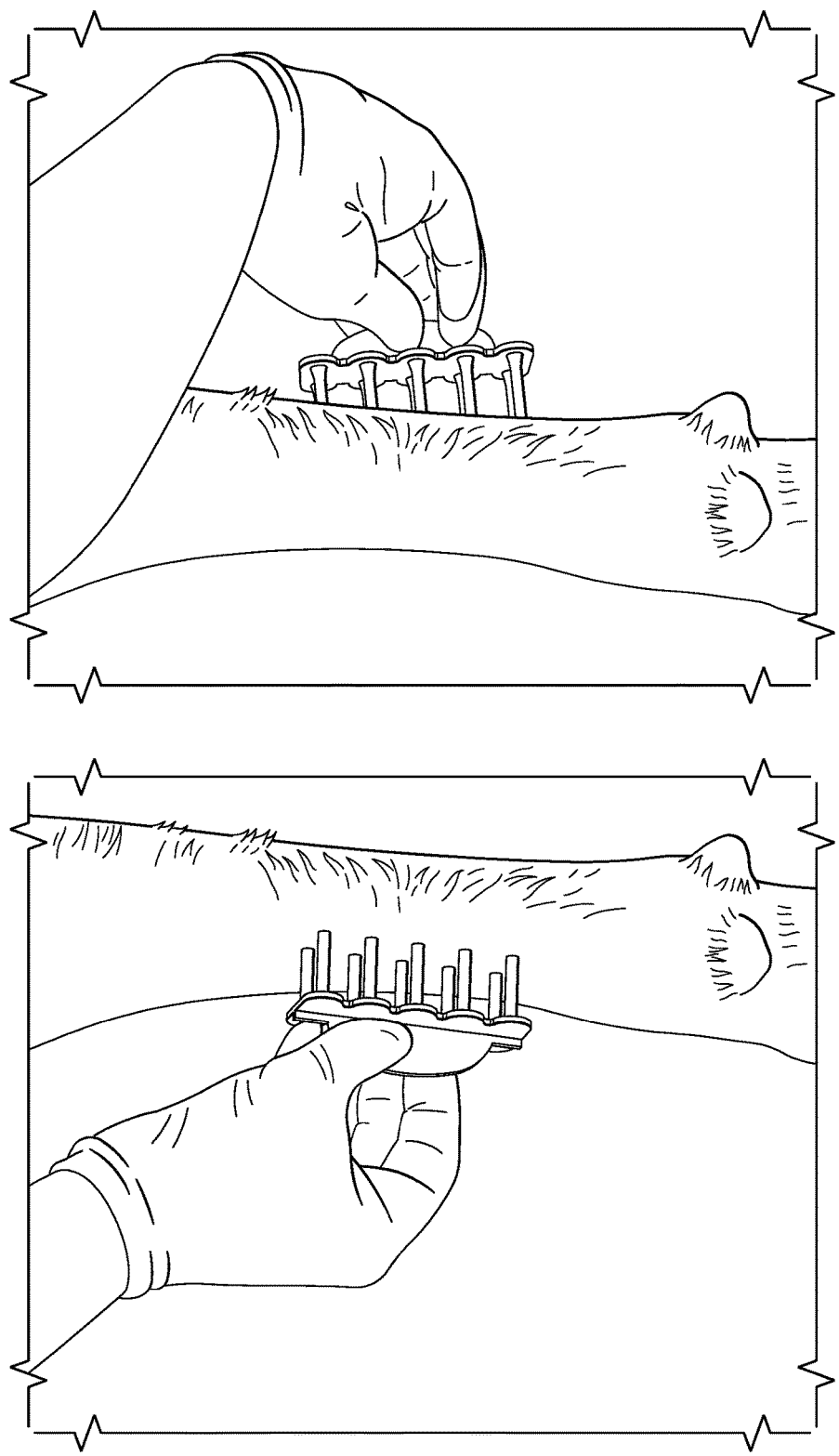
FIG. 3 shows a trans/intra dermal challenge site for inoculation to the lymph nodes.
Figure 4:
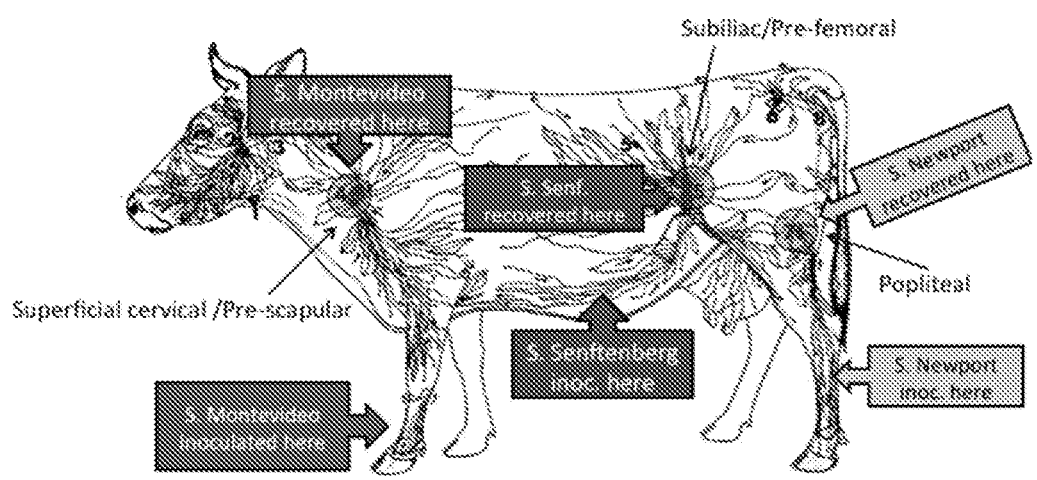
FIG. 4 shows the location of the inoculations and the lymph nodes from which the different strains of bacteria were recovered.

A second study was conducted identical to the above study with the exception that the challenge dose of *Salmonella* was lower ($10^7$ vs $10^8$) and the time frame between challenge and necropsy extended. Lymph nodes collected on 14 and 28 d post-challenge (16 steers) were all culture negative, therefore the study was terminated and future oral challenge models will employ a higher challenge dose and/or multiple challenges. A third pilot study was recently initiated to determine if intra-dermal application of *Salmonella* is capable of infecting non-mesenteric lymph nodes. Early results were positive and the potential model is currently under further investigation. FIG. 4 shows the location of the inoculations and the lymph nodes from which the different strains of bacteria were recovered.

Example 2: Development of a Transdermal *Salmonella* Challenge Model in Calves

Recent investigations have found that *Salmonella* can be routinely recovered from peripheral lymph nodes (PLNs) of cattle presented for harvest. When contained within the PLNs, this foodborne pathogen is protected from currently used postharvest, in-plant intervention strategies and, therefore, PLNs harboring *Salmonella* may be a potential contaminant of ground beef. The objective of this work was to develop a challenge model that effectively and repeatedly results in *Salmonella*-positive PLNs. A 10-lancet skin-allergy instrument was inoculated with *Salmonella*, and calves were inoculated intra- and/or transdermally by applying the device over various ventral regions of the skin. *Salmonella* was successfully and predictably recovered from region-specific PLNs up to 8 days postchallenge. Furthermore, serotypes inoculated within specific regions were only recovered from the PLNs draining those regions. This model provides a method to predictably infect PLNs with *Salmonella*. Further, this model makes it possible to determine the duration of infection and to evaluate candidate interventions that may shorten the duration of infection.

Recent reports indicate that it is not uncommon to recover *Salmonella* from the peripheral lymph nodes (PLNs) of cattle presented for harvest (1, 6); moreover, others have implicated *Salmonella*-positive PLNs as a likely source of *Salmonella* in ground beef (7). Because *Salmonella* is a gastrointestinal pathogen (2-4), it seems logical that PLN infection by *Salmonella* occurs via systemic spread from the gastrointestinal tract. This hypothesized route has been supported by studies in which *Salmonella* was isolated from the mesenteric lymph nodes of healthy cattle at slaughter (10) and systemic translocation of *Salmonella* from the small intestine was found to occur via the lymphatic system (8, 9). However, recent attempts in the inventors' laboratory to develop a model of *Salmonella* infection of the PLNs using an oral challenge (5) have produced inconsistent and, therefore, unpredictable results.

It is possible that *Salmonella* may infect PLNs, whereby *Salmonella* crosses the host's integument transdermally. This may occur as a consequence of abrasions, diseases of the integument, or other means such as biting flies, whereby *Salmonella* is introduced intradermally or transdermally and then transported from the interstitial spaces to the regional draining PLNs. The present invention includes a model in which *Salmonella* is challenged either intradermally or transdermally may provide a more consistent infection of PLNs. The objective of this study was to develop and evaluate the intra- and transdermal routes of inoculation as potential models of PLN infection with *Salmonella*.

Materials And Methods. Care, use, and handling of experimental animals were preapproved by the Animal Care and Use Committee of the Food and Feed Safety Research Laboratory, U.S. Department of Agriculture. Because of the unknowns associated with a transdermal route of inoculation and because these studies are necessarily terminal in nature, a series of studies were developed to provide proof of principle and subsequent model development while limiting the number of animals involved. All steers were individually penned in covered, concrete floored pens with feed (hay and grain) and ad libitum water to meet the animal's nutritional requirements.

Study I. Of five Holstein steers (approximate body weight 635 kg), three were inoculated with *Salmonella* and two were controls. Animals were restrained in a squeeze chute, and each leg was immobilized. *Salmonella* inocula were injected intradermally above the metacarpus and metatarsus using a 1.0-ml tuberculin syringe fitted with a 22-gauge, 1.5-in. needle. Tryptic soy broth (TSB, 1 ml) containing the *Salmonella* ($10^8$ CFU *Salmonella* per ml) or corn oil (control) was administered in a series of five injections (0.2 ml per injection site) in each of the four legs. Four serovars were used: pansusceptible *Salmonella* Montevideo was inoculated in the right foreleg, multidrug-resistant (MDR) *Salmonella* Newport in the left foreleg, MDR *Salmonella* Typhimurium in the right rear leg, and pansusceptible *Salmonella* Senftenberg in the left rear leg. Steers were necropsied 2, 3, and 4 days following treatment administration (one treated steer on day 2; one control and one treated steer on each of days 3 and 4). Steers were euthanized (Euthasol, Delmarva Laboratories, Inc., Midlothian, Va.), and the right and left subiliacs, popliteal, and superficial cervical nodes were collected, weighed, and cultured for the challenge strains of *Salmonella*.

TABLE 1

Concentration, prevalence (positive or negative), and serogroups of *Salmonella* isolates recovered from the peripheral lymph nodes of three steers inoculated intradermally in the lower legs with four different *Salmonella* serotypes (proof of principle study I)

| | | | Steer | | | | | |
|---|---|---|---|---|---|---|---|---|
| | | | No. 8 | | No. 20 | | No. 22 | |
| Leg | Inoculated serogroup | Lymph node | CFU/g | ± | CFU/g | ± | CFU/g | ± |
| Right fore | $C_1$ | Superficial Cervical | 3.4 2/2 $C_1$ | Pos 5/5 $C_1$ | 5.2 5/5 $C_1$ | Pos 5/5 $C_1$ | 4.6 5/5 $C_1$ | Pos 5/5 $C_1$ |

TABLE 1-continued

Concentration, prevalence (positive or negative), and serogroups of
Salmonella isolates recovered from the peripheral lymph nodes
of three steers inoculated intradermally in the lower legs with four
different Salmonella serotypes (proof of principle study I)

| | | | Steer | | | | | |
| | | | No. 8 | | No. 20 | | No. 22 | |
| Leg | Inoculated serogroup | Lymph node | CFU/g | ± | CFU/g | ± | CFU/g | ± |
| --- | --- | --- | --- | --- | --- | --- | --- | --- |
| Right hind | B | Popliteal | 4.2 | Pos | 5.3 | Pos | 4.7 | Pos |
| | | | | 5/5 B | 5/5 B | 5/5 B | 5/5 B | 5/5 B |
| Left fore | $C_2$ | Subiliac | Neg | Neg | Neg | Neg | Neg | Neg |
| | | Superficial cervical | 3.6 3/3 $C_2$ | Pos 5/5 $C_2$ | 4.4 5/5 $C_2$ | Pos 5/5 $C_2$ | 4.5 5/5 $C_2$ | Pos 5/5 $C_2$ |
| Left hind | $E_4$ | Popliteal | Neg | Pos 5/5 $E_4$ | 2.9 1/1 $E_4$ | Pos 5/5 $E_4$ | 3.7 5/5 $E_4$ | Pos 5/5 $E_4$ |
| | | Subiliac | Neg | Neg | Neg | Neg | Neg | Neg |

Study II. One Holstein steer (approximate body weight 150 kg) was utilized to evaluate an alternative method for intradermal inoculation of Salmonella. A 10-microlancet, skin allergy testing instrument (ComforTen Multiple Skin Test Device, Hollister-Stier Allergy, Spokane, Wash.) was dip inoculated with MDR Salmonella Typhimurium (TSB with $4.5|10^8$/ml Salmonella) or pansusceptible Salmonella Senftenberg (TSB with $3.8|10^8$/ml Salmonella). The instrument is designed to penetrate intradermally, not subcutaneously. The inoculated instrument was applied with light pressure both medially and laterally (twice each) above the metacarpus and metatarsus of the steer; Salmonella Typhimurium was inoculated in the right legs and Salmonella Senftenberg in the left legs. In between applications (i.e., four applications per leg), the 10-lancet instrument was redipped into the appropriate Salmonella broth, and a new instrument was used for each leg. Two days following Salmonella challenge, the steer was euthanized and necropsied as above and Salmonella was cultured.

Study III. Two Holstein steers (approximate body weight 180 kg) were used to further examine the suitability of the 10-lancet inoculation instrument. Each steer was challenged with MDR Salmonella Newport (instrument was dip inoculated into TSB with 1.9 to $3.7|10^8$ Salmonella per ml) administered to each leg (five instrument applications per leg; one anterior and two each on medial and lateral sides of metacarpus and metatarsus). Each leg was inoculated at different times, with the right fore, right rear, left fore, and left rear legs inoculated 2, 4, 6, and 8 days prior to necropsy, respectively. Steers were euthanized and lymph nodes harvested as described above.

Lymph node processing and bacterial culture. Lymph nodes were transferred to the laboratory within 30 min of collection and processed as described previously (1). Tetrathionate broth (20 ml) was added to each sample bag containing the processed lymph node and was mixed for 60 s. For quantitative estimation, 1 ml of the pulverized lymph node-tetrathionate broth mixture was removed and 50 ml was direct plated on xylose lysine deoxycholate agar using a commercially available spiral plater (Spiral Biotech Autoplate 4000, Advanced Instruments, Inc., Norwood, Mass.). Plates were incubated (37° C., 24 h), followed by an additional 24 h at room temperature. Black colonies were counted and converted to log CFU per gram lymph node tissue. Following spiral plating, an additional 80 ml of tetrathionate broth was added and the lymph node-tetrathionate mixture was incubated overnight (37° C.). Then 100 ml of the enrichment was transferred to 5 ml of Rappaport-Vassiliadis broth and incubated at 42° C. for 24 h, prior to plating on brilliant green agar supplemented with novobiocin (25 mg/ml). Plates were incubated (37° C., overnight), and presumptive Salmonella isolates were serogrouped (five isolates per positive sample) using slide agglutination with Salmonella antiserum (Difco Laboratories, Detroit, Mich.).

Results. The intradermal route of inoculation described herein predictably resulted in Salmonella-positive PLNs. In the first study, the majority of PLNs examined in the three Salmonella-treated steers were culture positive for the specific challenge strains, and most contained significant quantifiable concentrations (2.9 to 5.3 log CFU/g lymph node tissue; Table 1). The exceptions were that all subiliac lymph nodes were culture negative. Furthermore, the route of inoculation provided excellent serotype-region specificity; the inventors only recovered the serotype (represented by distinct serogroups) from the PLNs that drain the region of inoculation. We did not recover any Salmonella from the PLNs of the two control steers. Mild to moderate swelling and lameness were observed in the steers inoculated with Salmonella but not in the controls. Although every effort was made to administer the Salmonella intradermally, controlling the depth of the injection using the tuberculin syringe was difficult.

Because of the challenge using the syringe and lameness issues, the inventors then used the 10-microlancet instrument. No swelling or lameness was observed following the use of this instrument; furthermore, it required minimal animal restraint and improved the ease of application. Use of this instrument in the second proof of principle study resulted in recovery of Salmonella from both the left popliteal and left superficial cervical PLNs, whereas those of the right legs and the subiliac nodes were culture negative (data not shown). In contrast to the first study, however, the concentration of Salmonella within the PLNs was below the limit of quantification. Isolates cultured from the lymph nodes of the left leg all belonged to serogroup B, the same serogroup administered to the left legs. Results from the third proof of principle study were similar to the second. In one steer, Salmonella was recovered from both right and left superficial cervical and popliteal PLNs; in the other steer, Salmonella was only recovered from the left superficial cervical PLNs (Table 2). None of the PLNs contained quantifiable Salmonella populations. All lymph node isolates belonged to serogroup C2, the same serogroup used to inoculate all legs in both animals. Salmonella was recovered from the lymph nodes at 2, 4, 6, and 8 days postinoculation. All subiliac lymph nodes were culture negative.

TABLE 2

*Salmonella* recovery (concentration, prevalence [positive or negative], and isolate serogroup) from the peripheral lymph nodes in steers receiving intradermal administration of *Salmonella* in the lower legs and necropsied 2, 4, 6, or 8 days postinoculation (proof of principle study III)

| Leg | Inoculated serogroup | Days Postinoculation | Lymph node | Steer No. 33 Concn | ± | Steer No. 35 Concn | ± |
|---|---|---|---|---|---|---|---|
| Right fore | $C_2$ | 2 | Superficial cervical | Neg | Pos 5/5 $C_2$ | Neg | Neg |
| Right hind | $C_2$ | 4 | Popliteal | Neg | Pos 5/5 $C_2$ | Neg | Neg |
| | | | Subiliac | Neg | Neg | Neg | Neg |
| Left fore | $C_2$ | 6 | Superficial cervical | Neg | Pos 5/5 $C_2$ | Neg | Pos 5/5 $C_2$ |
| Left hind | $C_2$ | 8 | Popliteal | Neg | Pos 5/5 $C_2$ | Neg | Neg |
| | | | Subiliac | Neg | Neg | Neg | Neg |

The present inventors describe the development of a challenge model that predictably results in *Salmonella*-positive PLNs. The intradermal route of inoculation is novel and somewhat unconventional, but the inventors believe it is an appropriate approach to determine that a proportion of the *Salmonella* observed in PLNs of cattle presented for harvest in the United States crosses the integument transdermally. This model provides distinct advantages over other routes of infection used, such as oral or intravenous. First, this route of inoculation predictably results in *Salmonella*-positive PLNs for at least 8 days postinoculation. With this approach, an estimate of the duration of infection can be made, and the impact of interventions, such as a vaccine, on the duration of infection can be evaluated. Duration of infection is an important biological attribute because prevalence, e.g., prevalence of *Salmonella*-positive PLNs in cattle presented for harvest, is a function of incidence and duration of infection. Incidence, rate of new PLN infections per unit time, is difficult to measure directly in real-world settings, but it can be estimated if the duration of infection is known. A further advantage is that this model allows examination of the effect of an intervention against multiple serotypes within an individual animal and the individual can serve as its own control, given the regional specificity of inoculation and recovery. This salient observation will reduce the number of animals required in future challenge models.

The 10-microlancet instrument is that a single-day inoculation resulted in concentrations of *Salmonella* within PLNs that were below the limit of quantification, yet this approach did not result in lameness or swelling and was well tolerated by the animals. On the other hand, the syringe application provided predictably quantifiable concentrations of *Salmonella* in the regional PLNs, but unfortunately, this method of inoculation (and the amount of inoculum) resulted in overt lameness and swelling and was difficult to administer. A further limitation of the approaches described herein is that none of the subiliac PLNs were positive for *Salmonella* following inoculation. This may be viewed as an important shortcoming since most of the work demonstrating recovery of *Salmonella* from PLNs of cattle presented for harvest has used the subiliac PLNs. In a companion paper (5), however, the inventors describe the use of a 10-microlancet instrument to inoculate *Salmonella* intradermally over the ventral abdomen region, resulting in predictably positive subiliac PLNs.

The studies described demonstrate the use of the present invention despite the number of animals in each study. Animals of different sizes were used. Despite the number of animals and the various sizes, the intradermal route of inoculation proved to be predictable and a suitable challenge model to result in *Salmonella*-positive PLNs. However, the excellent specificity of the serogroups recovered to those of the regionally inoculated strains suggests that prior exposure is not a high probability.

Example 3: Development of Challenge Models to Evaluate the Efficacy of a Vaccine to Reduce Carriage of *Salmonella* in Peripheral Lymph Nodes of Cattle Because challenge models to infect peripheral lymph nodes (PLNs) with *Salmonella* have not been reported, the inventors performed a series of studies to develop and refine challenge models to evaluate an intervention applied at the animal level and to provide initial estimates of efficacy of an intervention (i.e., a vaccine) to aid in the design of future studies. In each of four studies, steers (control or vaccinated) were inoculated with *Salmonella* strains Montevideo or Newport, and in study IV, *Salmonella* Senftenberg was also used. Calves were euthanized 14 to 42 days postinoculation, and PLNs were collected. In the first study, calves were challenged with, $10^{10}$ *Salmonella* cells, and few treatment differences were observed 14 days postchallenge. However, by day 21, *Salmonella* Newport was recovered from fewer vaccinated calves than control calves (P<0.05). In study II, calves were challenged with, $10^7$ *Salmonella* cells and, after two necropsies (14 and 28 days postchallenge), only one lymph node was *Salmonella* positive; therefore, the study was terminated. In study III, calves were again challenged with, $10^{10}$ *Salmonella* cells, and no significant effect of vaccine was observed in calves challenged with Montevideo or Newport strains. A transdermal route of challenge was explored in study IV, using a 10-lancet, allergy testing instrument. Sixteen steers were challenged with either *Salmonella* Newport or *Salmonella* Montevideo (*Salmonella* Newport right legs; *Salmonella* Montevideo left legs), and all steers were challenged on the lower abdomen with *Salmonella* Senftenberg. Transdermal inoculation resulted in predictably *Salmonella*-positive PLNs, and a modest vaccine effect was detected. Because it is well tolerated by the calves and results in predictable and regionally specific *Salmonella* recovery from PLNs, the transdermal route of challenge may be preferred by researchers wishing to evaluate the impact of interventions designed to reduce the carriage of *Salmonella* in PLNs.

Recent research suggests that *Salmonella* may be commonly harbored in peripheral lymph nodes (PLNs) of cattle presented for harvest (1, 7, 10). Because PLNs are frequently included in ground beef, *Salmonella* carriage in PLNs likely results in some degree of *Salmonella* contamination of ground beef. It may be practical to remove large, easily accessible PLNs during harvest; however, it is impractical to remove all PLNs, as cattle have many small PLNs throughout their carcasses. It is possible that preharvest control of *Salmonella* may complement within-plant control efforts and reduce the likelihood of ground beef contamination. A vaccine containing siderophore receptors and porin proteins from *Salmonella* Newport was associated with reduced shedding of *Salmonella* in the feces of dairy cattle (6, 11). In another study (9) of this vaccine, no difference in fecal *Salmonella* prevalence was observed, although the *Salmonella* prevalence and study design did not lend itself to such a comparison. No differences were observed in fecal shedding of *Salmonella* in studies of feedlot cattle (2) or dairy cows (8). It is possible, however, that immunity against *Salmonella* may reduce the duration of infection within lymph nodes regardless of an effect, or lack thereof, within the lumen of the intestine. If so, this vaccine may reduce the prevalence of *Salmonella* within the PLNs of cattle presented for harvest.

Because challenge models to infect PLNs with *Salmonella* have not been reported, the inventors performed a series of four studies to develop and refine challenge models that can be used to evaluate an intervention applied at the animal level and to provide initial estimates of efficacy of an intervention (i.e., a vaccine) that can be used by researchers to aid the design of future studies.

Materials And Methods. Care, use, and handling of experimental animals were preapproved by the Animal Care and Use Committee of the Food and Feed Safety Research Laboratory, U.S. Department of Agriculture. Recently weaned Holstein and Holstein-cross steers were purchased from a single supplier and transported to the laboratory in College Station, Tex. Upon arrival, steers were weighed, identified with an ear tag, and maintained in a large outside lot and fed a commercial nonmedicated calf starter and grass hay. In study I, symptoms of bovine respiratory disease were observed in most steers, and all were administered enrofloxacin (Baytril 100, Bayer Animal Health LLC, Shawnee Mission, Kans.). In subsequent studies, steers were metaphylactically administered tulathromycin (Draxxin, Pfizer Animal Health, New York, N.Y.) per manufacturer's recommendations upon arrival. Rectal swabs were collected weekly prechallenge and were cultured for *Salmonella*. Following acclimation (3 to 5 weeks), steers were randomly assigned to treatment (control or vaccine). Vaccinated steers were administered a commercially available *Salmonella* vaccine on days 0 and 21 per label directions (2 ml subcutaneous; *Salmonella* Newport Bacterial Extract vaccine with SRP Technology, Pfizer Animal Health, Madison, N.J.), whereas control animals received a sham injection of corn oil (2 ml subcutaneous). Steers were housed outdoors in covered, concrete floored pens, either two or four steers per pen, and were fed a diet to meet or exceed their nutritional requirements. Pens were washed daily. Steers were euthanized (Euthasol, Delmarva Laboratories, Midlothian, Va.), and the right and left subiliacs, popliteals, and superficial cervical nodes were collected, weighed, and cultured for the challenge strains of *Salmonella* as described below.

Study I. Thirty-two steers (average body weight 81 kg) were inoculated with either *Salmonella* Montevideo or *Salmonella* Newport in a 2|2 factorial design such that there were eight calves per treatment. Calves were challenged orally with 20 ml of tryptic soy broth (TSB) containing 1.0 and $1.2|10^{10}$ CFU of *Salmonella* Montevideo or *Salmonella* Newport, respectively. Body weights were collected weekly throughout the study period. Fourteen days postchallenge, one-half of the calves in each pen (and treatment) were euthanized and PLNs were collected. At 21 days postchallenge, all remaining calves were euthanized and PLNs were collected.

Study II. The design was similar to that of study I, except that the oral challenge included 4.2 and 6.0|107 CFU of *Salmonella* Montevideo and *Salmonella* Newport, respectively. Two calves per treatment were necropsied 14 and 28 days postchallenge. Due to the poor recovery of *Salmonella* from the PLNs, the study was terminated.

Study III. Using a design similar to that of studies I and II, calves were challenged with 1.5 and $1.3|10^{10}$ CFU of *Salmonella* Montevideo and *Salmonella* Newport, respectively, in 20 ml of TSB, and two calves per treatment were necropsied on days 14, 28, 35, and 42 postchallenge. In addition to the nodes described above, axillary lymph nodes (right and left) were collected.

Study IV. Sixteen steers (average body weight 193 kg; two per pen by treatment) were randomly allocated to vaccine or control treatment. Calves were challenged with either *Salmonella* Newport ($7.9|10^8$/ml; eight steers) or *Salmonella* Montevideo ($1.2|10^9$/ml; eight steers) using a 10-lancet allergy testing instrument (ComforTen Multiple Skin Test Device, Hollister-Stier Allergy, Spokane, Wash.) as described elsewhere (5). Four applications of this 10-lancet instrument were made to each leg; two applications were medial and two were lateral to the metacarpus-metatarsus, such that *Salmonella* Newport was challenged in the right legs and *Salmonella* Montevideo in the left legs. Additionally, all calves were challenged on the lower abdomen with *Salmonella* Senftenberg ($4.3|10^8$/ml) via two applications each on the right and left sides. A new instrument was used for the different serovars and for each calf. Three and 6 days following *Salmonella* challenge, one-half of the calves in each treatment were euthanized and PLNs were collected.

Lymph node processing. Within 15 min of collection, lymph nodes were transferred to the laboratory and each node was trimmed of excess fat and fascia. Trimmed lymph nodes were weighed and then surface sterilized by immersion in boiling water for 3 s. The sterilized lymph node was placed into a filtered stomacher bag, and the tissue was pulverized using a rubber mallet. Tetrathionate broth (20 ml) was added to each sample bag, followed by mixing for 60 s with a laboratory blender. For quantitative culture, 1 ml of the pulverized lymph node-tetrathionate broth mixture was removed and 50 ml was direct plated on xylose lysine deoxycholate agar using a commercially available spiral plater (Spiral Biotech Autoplate 4000, Advanced Instruments, Inc., Norwood, Mass.). Plates were incubated (37° C., 24 h) followed by an additional 24 h at room temperature. Black colonies were counted and converted to log CFU per gram PLN. Following spiral plating, an additional 80 ml of tetrathionate broth was added, and the lymph node-tetrathionate mixture was incubated overnight (37° C.). A sample (100 ml) of this enrichment was transferred to 5 ml of Rappaport-Vassiliadis broth and incubated at 42° C. for 24 h, and then it was plated for isolation on brilliant green agar supplemented with novobiocin (25 mg/ml). Plates were incubated at 37° C. overnight, and *Salmonella* isolates were serogrouped (three isolates per PLN). Serogrouping was conducted using slide agglutination with *Salmonella* antiserum (Difco, BD, Detroit, Mich.). Rectal swabs were enriched in 20 ml of tetrathionate broth and were incubated at 37° C. overnight; next, 100 ml was inoculated into 5 ml of Rappaport-Vassiliadis broth, incubated as above, and then plated for isolation on brilliant green agar supplemented with novobiocin and incubated as described. Statistical analysis. Data were analyzed using SAS software (version 9.3, SAS Institute Inc., Cary, N.C.). Contingency tables were developed and within-table dependency was evaluated using either a chi-square statistic or a Fisher's exact test. Logistic regression models were constructed to compare treatment effects.

Results. Rectal swabs collected prechallenge were all *Salmonella* negative except for study III, in which a few swabs were positive and all of the isolates belonged to serogroups different from the challenge strains. In study I, *Salmonella* was recovered from 58.3 and 87.5% of PLNs and calves, respectively. No significant differences were observed in the percentage of PLNs positive for *Salmonella* Montevideo or *Salmonella* Newport on day 14 (Table 3). At 21 days postinoculation, *Salmonella* Newport was recovered from fewer (P<0.05) PLNs among the vaccinated calves (4%) compared with the control calves (54%). With two exceptions, all recovered isolate serogroups matched the respective challenge strains. Two steers in the Montevideo (serogroup C1) treatment (one each control and vaccine) also had serogroup C2 isolates cultured from their lymph nodes.

TABLE 3

Prevalence of Salmonella serovars (Montevideo and Newport) in the peripheral lymph nodes of vaccinated or control calves necropsied 14 or 21 days postchallenge (Study I)[a]

| Lymph node | 14 days postchallenge (n = 16) | | | | 21 days postchallenge (n = 16) | | | |
|---|---|---|---|---|---|---|---|---|
| | Montevideo | | Newport | | Montevideo | | Newport | |
| | Control | Vaccine | Control | Vaccine | Control | Vaccine | Control | Vaccine |
| Subiliac | | | | | | | | |
| Right | 50 | 75 | $50_A$ | $100_B$ | 100 | 75 | 25 | 0 |
| Left | 50 | 75 | 75 | 100 | 100 | 75 | 50 | 25 |
| Popliteal | | | | | | | | |
| Right | 50 | 75 | 50 | 50 | 25 | 75 | $75_C$ | $0_D$ |
| Left | 50 | 50 | $50_A$ | $100_B$ | 100 | 75 | $50_A$ | $0_B$ |
| Superficial cervical | | | | | | | | |
| Right | 50 | 75 | $50_A$ | $100_B$ | 75 | 75 | $75_C$ | $0_D$ |
| Left | 50 | 50 | 50 | 50 | $50_C$ | $100_D$ | $50_A$ | $0_B$ |
| All nodes | 50 | 67 | $54_A$ | $83_B$ | 75 | 79 | $54_C$ | $4_D$ |

[a]Vaccine, administered a commercially available *Salmonella* vaccine;
Control, administered a sham injection. Values followed by letters $_A$ and $_B$ indicate that row percentages within necropsy and *Salmonella* strain tend to differ (P < 0.10);
values followed by letters $_C$ and $_D$ indicate that row percentages within necropsy and *Salmonella* strain are different (P < 0.05).

In study II, *Salmonella* was only recovered from two PLNs harvested during the first two necropsies (14 and 28 days postinoculation); therefore, the study was terminated. The higher challenge dose (i.e., $10^{10}$) in study III resulted in the recovery of *Salmonella* from PLNs. *Salmonella* was recovered from 35.2 and 62.5% of PLNs and calves, respectively. No significant treatment differences were observed, with one exception: the vaccine treatment decreased (P<0.05) the percentage of *Salmonella*-positive left axillary nodes compared with controls across serotypes. *Salmonella* was recovered from fewer PLNs of calves challenged with *Salmonella* Newport than from those challenged with *Salmonella* Montevideo (Table 4). The majority of isolates (98%) matched the serogroup of the challenge strain. The only exceptions were that *Salmonella* Montevideo was cultured from the popliteal and subiliac in one calf on day 35 and from the subiliac in another calf on day 42; both of these calves were inoculated with *Salmonella* Newport. In the transdermal challenge model (study IV), *Salmonella* was recovered from 58.3 and 93.8% of PLNs and calves, respectively. No treatment differences were observed among calves inoculated with *Salmonella* Montevideo, except that there was reduced (P<0.05) likelihood of recovery from the right subiliac lymph nodes among vaccinates compared with controls (Table 5). Across all nodes, the likelihood of recovery of *Salmonella* Newport from PLNs was lower (P=0.03) among vaccinated calves (33.3%) compared with controls (66.7%). All but one isolate matched the serogroup of regional challenge. The only exception was that one isolate from a subiliac lymph node was serogroup C2 (presumably Newport) instead of E4 (i.e., Senftenberg).

TABLE 4

Prevalence of *Salmonella* (Montevideo and Newport) in the peripheral lymph nodes of vaccinated or control calves (Study III)[a]

| Lymph node | Montevideo | | Newport | |
|---|---|---|---|---|
| | Control | Vaccine | Control | Vaccine |
| Subiliac | | | | |
| Right | 75 | 87.5 | 25 | 0 |
| Left | 75 | 62.5 | 25 | 12.5 |
| Popliteal | | | | |
| Right | 50 | 62.5 | 12.5 | 12.5 |
| Left | 37.5 | 62.5 | 0 | 12.5 |
| Superficial cervical | | | | |
| Right | 50 | 75 | 0 | 0 |
| Left | 50 | 75 | 0 | 0 |
| Axillary | | | | |
| Right | 50 | 62.5 | 0 | 0 |
| Left | 87.5 | 50 | 0 | 0 |
| All nodes | 56.3 | 70.8 | 10.4 | 6.3 |

[a]Vaccine, administered a commercially available *Salmonella* vaccine; Control, administered a sham injection.

DISCUSSION. In the work described herein, the inventors developed two distinct routes of *Salmonella* challenge that resulted in *Salmonella* recovery from PLNs. Because prevalence of *Salmonella* in PLNs is a function of incidence (i.e., rate of new PLN infections) and duration of infection, the inventors included various windows of harvest to capture a change in the duration of infection, given that the inventors attempted to control the incidence (i.e., by providing the challenge at one time point). In study I, the oral challenge, no evidence of a reduction in prevalence was observed 14 days after challenge. After 21 days, a decrease was observed in calves challenged with *Salmonella* Newport, which likely indicated an increased rate of clearance (or reduced duration of infection). Also, a treatment effect was observed in study IV (transdermal), and a numerical reduction was observed in study III. Despite this evidence supporting its efficacy against *Salmonella* Newport, no association (even with a liberal interpretation of P values) was observed for *Salmonella* Montevideo. This may be because there is a lack of antigenic homology between the challenge serotypes or because Montevideo has additional mechanisms for iron acquisition, or it may be due to other variations among host-bacteria interactions.

TABLE 5

Prevalence of *Salmonella*-positive lymph nodes in vaccinated or control calves following transdermal challenge of *Salmonella* to the lower legs and ventral abdomen (Study IV)[a]

| Node | Montevideo/ Senftenberg | | Newport/ Senftenberg | | Combined Stains | |
|---|---|---|---|---|---|---|
| | Control | Vaccine | Control | Vaccine | Control | Vaccine |
| Subiliac | | | | | | |
| Right | $75_A$ | $0_B$ | 25 | 25 | 50 | 12.5 |
| Left | 0 | 25 | 75 | 25 | 38 | 25 |
| Popliteal | | | | | | |
| Right | 75 | 100 | 75 | 50 | 75 | 75 |
| Left | 75 | 75 | 50 | 25 | 63 | 50 |
| Superficial cervical | | | | | | |
| Right | 75 | 100 | 75 | 75 | 75 | 88 |
| Left | 100 | 100 | $100_A$ | $0_B$ | $100_A$ | $50_B$ |
| All nodes | 67 | 67 | $67_C$ | $33_D$ | 67 | 50 |

[a]*Salmonella* strains Montevideo and Newport (n~16 calves each) were administered to the lower legs;
*Salmonella* Senftenberg (all calves) was administered to the ventral abdomen. Vaccine, administered a commercially available *Salmonella* vaccine;
Control, administered a sham injection. Values followed by letters $_A$ and $_B$ indicate that row percentages within *Salmonella* strain are different (P < 0.05);
values followed by letters $_C$ and $_D$ indicate that row percentages within *Salmonella* strain tend to differ (P ≤ 0.10). It is clear from the work described herein that a substantial oral dose (i.e., $10^{10}$) of *Salmonella* is required to result in recovery of *Salmonella* from PLNs. In study II, the lower dose failed to produce *Salmonella* in PLNs at detectable concentrations. On occasion, the inventors did recover serogroups other than the challenge serogroup. It may be that repeated lower doses would have been equally effective as (or even more effective than) a single large challenge. Whereas repeated exposures may better mimic real-world events, the inventors attempted to control incidence to the extent possible so that observed differences in vaccine status (or in serotype status) were primarily a reflection of changes in duration of infection. Once duration of infection is known for specific serotypes, variation in challenge regimens might be explored.

The recovery of serogroup C2 in calves challenged with *Salmonella* Montevideo (i.e., C1) (study I) and of C1 in calves challenged with *Salmonella* Newport (study III) may have resulted from cross-contamination via workers, flies, birds, air movement, or the environment. Alternatively, the inventors cannot rule out prior exposure, as these serotypes are frequently isolated from dairy cattle (3, 4, 12). A transdermal route of infection may account for some *Salmonella* recovered from the PLNs of cattle presented for harvest. The inventors shows a transdermal route of infection as the study IV challenge study. Multiple serotypes were used within the sample animal (i.e., Senftenberg and Montevideo or Senftenberg and Newport), and this route of challenge predictably resulted in positive PLNs. Moreover, the serogroups recovered from the PLNs that drain the challenge region (e.g., right foreleg to prescapular lymph node versus ventral abdomen to subiliac lymph node) matched in all but one instance. Similar to study I, a vaccine effect was observed for *Salmonella* Newport but not for *Salmonella* Montevideo.

Across all necropsy days, the relative magnitude of association between vaccine status and *Salmonella* Newport prevalence for studies I, III, and IV was 20.3, 39.4, and 50%, respectively. These data, in conjunction with the control prevalence, should inform the design and sample size calculations of future studies. While the ideal window in which to sample PLNs subsequent to challenge is not completely certain, the time periods described herein provide a reasonable estimate.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

References—Example 2

1. Arthur, T. M., D. M. Brichta-Harhay, J. M. Bosilevac, M. N. Guerini, N. Kalchayanand, J. E. Wells, S. D. Shackelford, T. L. Wheeler, and M. Koohmaraie. 2008. Prevalence and characterization of *Salmonella* in bovine lymph nodes potentially destined for use in ground beef J. Food Prot. 71:1685-1688.
2. Brichta-Harhay, D. M., T. M. Arthur, J. M. Bosilevac, N. Kalchayanand, S. D. Shackleford, T. L. Wheeler, and M. Koohmaraie. 2011. Diversity of multidrug-resistant *Salmonella enterica* strains associated with cattle at harvest in the United States. Appl. Environ. Microbiol. 77:1783-1796.
3. Brichta-Harhay, D. M., M. N. Guerini, T. M. Arthur, J. M. Bosilevac, N. Kalchayanand, S. D. Shackleford, T. L. Wheeler, and M. Koohmaraie. 2008. *Salmonella* and *Escherichia coli* O157:H7 contamination on hides and carcasses of cull cattle presented for slaughter in the United States: an evaluation of prevalence and bacterial loads by immunomagnetic separation and direct plating methods. Appl. Environ. Microbiol. 74:6289-6297.
4. Edrington, T. S., M. E. Hume, M. L. Looper, C. L. Schultz, A. C. Fitzgerald, T. R. Callaway, K. J. Genovese, K. M. Bischoff, J. L. McReynolds, R. C. Anderson, and D. J. Nisbet. 2004. Variation in the faecal shedding of *Salmonella* and *E. coli* O157:H7 in lactating dairy cattle and examination of *Salmonella* genotypes using pulsed-field gel electrophoresis. Lett. Appl. Microbiol. 38:366-372.
5. Edrington, T. S., G. H. Loneragan, J. Hill, K. J. Genovese, D. M. Brichta-Harhay, R. L. Farrow, N. A. Krueger, T. R. Callaway, R. C. Anderson, and D. J. Nisbet. 2013. Development of challenge models to evaluate the efficacy of a vaccine to reduce carriage of *Salmonella* in peripheral lymph nodes of cattle. J. Food Prot. 76:1259-1263.
6. Haneklaus, A. N., K. B. Harris, D. B. Griffin, T. S. Edrington, L. M. Lucia, and J. W. Savell. 2012. *Salmonella* prevalence in bovine lymph nodes differs among feedyards. J. Food Prot. 75:1131-1133.
7. Koohmaraie, M., J. A. Scanga, M. J. De La Zerda, B. Koohmaraie, L. Topay, V. Beskhlebnaya, T. Mai, K. Greeson, and M. Samadpour. 2012. Tracking the sources of *Salmonella* in ground beef produced from nonfed cattle. J. Food Prot. 75:1464-1468.
8. Paulin, S. M., P. R. Watson, A. R. Benmore, M. P. Stevens, P. W. Jones, B. Villarreal-Ramos, and T. S. Wallis. 2002. Analysis of *Salmonella enterica* serotype-host specificity in calves: avirulence of S. enteric serotype Gallinarum correlates with bacterial dissemination from mesenteric lymph nodes and persistence in vivo. Infect. Immun. 70:6788-6797.
9. Pullinger, G. D., S. M. Paulin, B. Charleston, P. R. Watson, A. J. Bowen, F. Dziva, E. Morgan, B. Villarreal-Ramos, T. S. Wallis, and M. P. Stevens. 2007. Systemic translocation of *Salmonella enterica* serovar Dublin in cattle occurs predominantly via efferent lymphatics in a cell-free niche and requires type III secretion system 1 (T3SS-1) but not T3SS-2. Infect. Immun. 75:5191-5199.
10. Samuel, J. L., D. A. O'Boyle, W. J. Mathers, and A. J. Frost. 1979. Isolation of *Salmonella* from mesenteric lymph nodes of healthy cattle at slaughter. Res. Vet. Sci. 28:368-372.

References—Example 3

1. Arthur, T. M., D. M. Brichta-Harhay, J. M. Bosilevac, M. N. Guerini, N. Kalchayanand, J. E. Wells, S. D. Shackelford, T. L. Wheeler, and M. Koohmaraie. 2008. Prevalence and characterization of *Salmonella* in bovine lymph nodes potentially destined for use in ground beef. J. Food Prot. 71:1685-1688.
2. Dodd, C. C., D. G. Renter, D. U. Thomson, and T. G. Nagaraja. 2011. Evaluation of the effects of a commercially available *Salmonella* Newport siderophore receptor and porin protein vaccine on fecal shedding of *Salmonella* bacteria and health and performance of feedlot cattle. Am. J. Vet. Res. 2:239-247.
3. Edrington, T. S., T. R. Callaway, R. C. Anderson, and D. J. Nisbet. 2008. Prevalence of multidrug-resistant *Salmonella* on commercial dairies utilizing a single heifer raising facility. J. Food Prot. 71:27-34.
4. Edrington, T. S., B. H. Carter, T. H. Friend, G. R. Hagevoort, T. L. Poole, T. R. Callaway, R. C. Anderson, and D. J. Nisbet. 2009. Influence of sprinklers, used to alleviate heat stress, on faecal shedding of *E. coli* O157: H7 and *Salmonella* and antimicrobial susceptibility of *Salmonella* and *Enterococcus* in lactating dairy cattle. Lett. Appl. Microbiol. 48:738-743.
5. Edrington, T. S., G. H. Loneragan, J. Hill, K. J. Genovese, H. He, T. R. Callaway, R. C. Anderson, D. M. Brichta-Harhay, and D. J. Nisbet. 2013. Development of a transdermal *Salmonella* challenge model in calves. J. Food Prot. 76:1255-1258.
6. Farrow, R. L. 2012. Quantitative herd-level evaluation of a commercially available vaccine for control of *Salmonella* in dairy cattle. Ph.D. dissertation. Texas A&M University, College Station.
7. Haneklaus, A. N., K. B. Harris, D. B. Griffin, T. S. Edrington, L. M. Lucia, and J. W. Savell. 2012. *Salmonella* prevalence in bovine lymph nodes differs among feedyards. J. Food Prot. 75:1131-1133.
8. Heider, L. C., R. W. Meiring, A. E. Hoet, W. A. Gebreyes, J. A. Funk, and T. E. Wittum. 2008. Evaluation of vaccination with a commercial subunit vaccine on shedding of *Salmonella enterica* in subclinically infected dairy cows. J. Am. Vet. Med. Assoc. 233:466-469.
9. Hermesch, D. R., D. U. Thomson, G. H. Loneragan, D. R. Renter, and B. J. White. 2008. Effects of a commercially available vaccine against *Salmonella enterica* serotype Newport on milk production, somatic cell count, and shedding of *Salmonella* organisms in female dairy cattle with no clinical signs of salmonellosis. Am. J. Vet. Res. 9: 1229-1234.
10. Koohmaraie, M., J. A. Scanga, M. J. De La Zerda, B. Koohmaraie, L. Tapay, V. Beskhlebnaya, T. Mai, K. Greeson, and M. Samadpour. 2012. Tracking the sources of *Salmonella* in ground beef produced from nonfed cattle. J. Food Prot. 75:1464-1468.
11. Loneragan, G. H., D. U. Thomson, R. M. McCarthy, H. E. Webb, A. E. Daniels, T. S. Edrington, D. J. Nisbet, S. J. Trojan, S. C. Rankin, and M. M. Brashears. 2012. *Salmonella* diversity and burden in cows on and culled from dairy farms in the Texas high plains. Foodborne Pathog. Dis. 9:549-555.
12. U.S. Department of Agriculture, Food Safety and Inspection Service. 2010. Progress report on *Salmonella* testing of raw meat and poultry products, 1998-2010. Available at: www.fsis.usda.gov/PDF/*Salmonella*_Progress_Report_1998-2003.pdf. Accessed 10 Apr. 2013.

What is claimed is:

1. A method of observing and evaluating bacterial infections within the lymph nodes of animals presented for harvest comprising:
inoculating intradermally with a device capable of inoculating concurrently at multiple sites an animal with a known amount of a bacterial pathogen, wherein the multiple inoculation sites comprise lymph node drainage areas, wherein the bacterial pathogen that is a live bacterial pathogen selected from *Salmonella, Listeria, Shigella, Fransicella, Clostridum, Staphylococcus, Streptococcus*, or *Bacillus*; and
at one or more time points obtaining one or more lymph node biopsies are aseptically harvested to determine the extent of the bacterial pathogen in the lymph nodes.

2. The method of claim 1, wherein the inoculation is subdermal.

3. The method of claim 1, wherein the lymph node drainage areas comprise at least one of subiliac, popliteal, retropharangeal, superficial cervical, and mesenteric.

4. The method of claim 1, wherein the animals comprise bovine, equine, ovine, porcine, or caprine.

5. The method of claim 1, wherein the bacterial pathogen is selected from *Salmonella* Newport and Montevideo.

6. A method of observing and evaluating bacterial infections within the lymph nodes of animals presented for harvest comprising:
inoculating intradermally with a multi inoculator at one or more sites of an animal a known amount of a bacterial pathogen, wherein the one or more inoculation sites comprise lymph node drainage areas, wherein the bacterial pathogen is a live bacterial pathogen selected from *Salmonella, Listeria, Shigella, Fransicella, Clostridum, Staphylococcus, Streptococcus*, or *Bacillus*;
treating the animal with one or more therapies, treatments, or exposure;
at one or more time points obtaining one or more lymph node biopsies are aseptically harvested to determine the extent of the bacterial pathogen in the lymph nodes; and
determining if the one or more therapies, treatments, or exposure were effective to eliminate or reduce the bacterial pathogen.

7. The method of claim 6, wherein the inoculation is subdermal.

8. The method of claim 6, wherein the lymph node drainage areas comprise at least one of subiliac, popliteal, retropharangeal, superficial cervical, and mesenteric.

9. The method of claim 6, wherein the animals comprise bovine, equine, ovine, porcine, or caprine.

10. The method of claim 6, wherein the bacterial pathogen is selected from *Salmonella* Newport and Montevideo.

11. A method of testing a compound for elimination of bacterial infections within the lymph nodes of animals presented for harvest comprising:

> inoculating intradermally with a multi inoculator at one or more sites of an animal a known amount of a bacterial pathogen, wherein the one or more inoculation sites comprise lymph node drainage areas, wherein the bacterial pathogen that is a live bacterial pathogen selected from *Salmonella, Listeria, Shigella, Fransicella, Clostridum, Staphylococcus, Streptococcus*, or *Bacillus*;
>
> treating the animal with one or more compounds;
>
> at one or more time points obtaining one or more lymph node biopsies are aseptically harvested to determine the extent of the bacterial pathogen in the lymph nodes; and
>
> determining if the compound was effective to eliminate or reduce the bacterial pathogen.

12. The method of claim 11, wherein the inoculation is subdermal.

13. The method of claim 11, wherein the lymph node drainage areas comprise at least one of subiliac, popliteal, retropharangeal, superficial cervical, and mesenteric.

14. The method of claim 11, wherein the animals comprise bovine, equine, ovine, porcine, or caprine.

15. The method of claim 11, wherein the bacterial pathogen is selected from *Salmonella* Newport and Montevideo.

* * * * *